United States Patent
Hogan et al.

[11] Patent Number: 6,117,479
[45] Date of Patent: Sep. 12, 2000

[54] ELECTROSTATIC COATING

[75] Inventors: John E. Hogan, Faversham; John N. Stantiforth; Linda Reeves, both of Bath; Trevor Page, Southampton, all of United Kingdom

[73] Assignee: Phoqus Limited, Kent, United Kingdom

[21] Appl. No.: 08/999,564

[22] Filed: Nov. 10, 1997

[30] Foreign Application Priority Data

May 9, 1995 [GB] United Kingdom .................... 9509347
Oct. 5, 1995 [GB] United Kingdom .................... 9520302

[51] Int. Cl.$^7$ ...................................................... B05D 1/04
[52] U.S. Cl. ......................... 427/2.14; 427/475; 427/477; 427/481; 427/485
[58] Field of Search ..................................... 427/475, 477, 427/481, 482, 485, 2.14; 118/16, 630

[56] References Cited

U.S. PATENT DOCUMENTS

| | | |
|---|---|---|
| 2,698,814 | 1/1955 | Ransburg . |
| 3,900,000 | 8/1975 | Gallen . |
| 4,176,175 | 11/1979 | Maekawa et al. . |
| 4,433,076 | 2/1984 | Bauer et al. . |
| 4,482,387 | 11/1984 | Wood et al. . |
| 4,547,571 | 10/1985 | Mukohyama et al. . |
| 4,704,295 | 11/1987 | Porter et al. . |
| 5,206,030 | 4/1993 | Wheatley et al. . |

FOREIGN PATENT DOCUMENTS

| | | |
|---|---|---|
| 0 063 014 | 10/1982 | European Pat. Off. . |
| 0 307 642 A2 | 3/1989 | European Pat. Off. . |
| 307 642 | 3/1989 | European Pat. Off. . |
| 0 551 700 A1 | 7/1993 | European Pat. Off. . |
| 0 567 201 A2 | 10/1993 | European Pat. Off. . |
| 0 607 009 A1 | 7/1994 | European Pat. Off. . |
| 2 247 701 | 4/1974 | Germany . |
| 3049179 A1 | 7/1982 | Germany . |
| 1075404 | 7/1967 | United Kingdom . |
| 2 065 691 | 7/1981 | United Kingdom . |
| 2 253 164 | 9/1992 | United Kingdom . |
| 92/11002 | 7/1992 | WIPO . |
| 92/14451 | 9/1992 | WIPO . |
| 96/02236 | 2/1996 | WIPO . |
| 96/39256 | 12/1996 | WIPO . |
| 96/39257 | 12/1996 | WIPO . |
| 97/04827 | 2/1997 | WIPO . |
| 97/37775 | 10/1997 | WIPO . |
| 97/37803 | 10/1997 | WIPO . |
| 97/38480 | 10/1997 | WIPO . |

OTHER PUBLICATIONS

Kirk–Othmer Encyclopedia of Chemical Technology vol. 19, 3$^{rd}$ Ed. p. 1–2, 1982.
Chemical Abstracts, vol. 120, No. 20, (1994), Grosvenor M.P.
Diss. Abstr. Int., vol. 53, No. 7 (1991) Bath, p. 3492, Grosvenor M.P.

*Primary Examiner*—Fred J. Parker
*Attorney, Agent, or Firm*—Nixon & Vanderhye

[57] ABSTRACT

Method of electrostatically coating a substrate wherein the substrate is brought to a coating station at which it is held substantially electrically isolated from its surroundings adjacent a source of particulate coating material. The substrate and the coating material are held at a potential difference to each other sufficient to coat the exposed surface of the substrate with particles of coating material.

84 Claims, 2 Drawing Sheets

ELECTROSTATIC COATING

The present invention relates to a method and apparatus for the electrostatic coating of electrically poorly conducting substrates. It finds particular application in the coating of solid pharmaceutical dosage forms such as tablet cores, capsules, granules and beads with particulate coating materials, including powders and droplets of liquid.

BACKGROUND OF THE INVENTION

The use of electrostatic techniques to coat electrically conductive substrates, such as metal objects, is well known and successful. The coating, such as droplets of liquid paint, is electrically charged by applying a potential difference to it and is attracted to the earthed substrate.

The conventional electrostatic coating technigue described above has not been successfully applied to the coating of pharmaceutical tablet cores or other poor electrical conductors, generally those with a resistivity of more than $10^{10}$–$10^{15}$ $\Omega$m. Proposals have been made in which tablet cores are earthed, and a powdered coating material is directed at them through a nozzle which imparts an electrical charge to the powder. The powder coating is then fused to give a uniform coat. This method has been found inefficient, since adequate earthing of the cores has not been achieved, and the charge on the powder accumulates on the surface of the cores, repelling further charged powder. Even if the cores are carried on for example an earthed conveyor belt, the poorly conducting nature of the cores allows charge to build up.

Further, the bulk of the powder (95% in the case of corona charging) is uncharged, and does not land or stay on the cores, and must either be recovered or wasted. These difficulties lead to non-uniformity in the weight and thickness of the coating applied to the cores. This is pharmaceutically unacceptable, in particular when the core coating plays a significant role in the timing of the release of the pharmaceutical into the body after ingestion.

Improvements have been proposed, for example in WO 92/14451 which proposes moistening the cores with water prior to spraying with the charged powder, to improve the earthing of the surfaces of the cores and to encourage the powder, once on the surfaces, to remain. Even with these improvements, coating remains inherently inefficient; powder is wasted and the time necessary for complete coating is too long for efficient production.

SUMMARY OF THE INVENTION

The present invention overcomes these problems by providing in accordance with a first aspect a method for electrostatically coating an electrically poorly conducting substrate comprising bringing the substrate to a coating station at which it is held electrically isolated from, and preferably at a potential difference to, its surroundings adjacent a source of particulate coating material, the substrate and the coating material being held at a potential difference to each other sufficient to coat the exposed surface of the substrate with particles of coating material. Preferably, the substrate is held at a potential.

It is particularly preferred that the electric field between the coating material and the substrate is shaped. The field can be shaped so that the substrate is in a potential well. That is, the substrate is surrounded by a potential different to its own, there being a sharp cut-off between the two potentials. Thus, substantially all the coating material is attracted to the substrate, reducing waste of the coating material and avoiding the problems associated with coating material falling on the substrate surroundings.

Shaping of the field is achieved by manipulation of the potential difference between the substrate, its surroundings and the coating material. For example, a substrate is carried by but insulated from a surface, the surface being held at the same potential as the coating material while the substrate is held at a different potential to that of the coating material. Coating material is therefore attracted to the substrate and not to the surface.

Preferably, substantially the only motive force between the substrate and the coating material is electrostatic. It may be desirable to provide particulate coating material in the form of a cloud of particles, formed for example by fluidising a bed of the coating material. Also preferably, the substrate is supported on an electrode while being electrically isolated from its surroundings.

For powder coating applications, the substrate may be brought to a pretreatment station at which the exposed surface of the substrate is coated with a capture-enhancing liquid. After coating with the coating material, the substrate can be brought to a heating station where the coating material if powder is fused or if liquid is dried to an effectively continuous uniform coating. The reverse surfaces of the substrate can then be coated in the same way with the same coating material as the first-coated surface or with a different material. In this way, for example bi-coloured coated substrates may be produced. Preferably, the method is carried out continuously.

It is preferred that powders used in the method according to the invention has a resistivity greater than $10^8$ $\Omega$m, preferably between $10^8$ and $10^{15}$ $\Omega$m.

There is provided in accordance with a second aspect of the invention apparatus for electrostatically coating an electrically poorly conducting substrate comprising a coating station at which the substrate is substantially electrically isolated from, and preferably at a potential difference to, its surroundings adjacent means for supplying a particulate coating material, and means for holding a substrate and a coating material at a potential difference to each other. Preferably, the substrate is held at a potential.

Preferably, the apparatus further comprises an electric field shaping device adjacent the substrate. Particulary preferably, the electric field shaping device surrounds the substrate.

The apparatus advantageously includes an electrically conductive support surface such as a drum electrically isolated from the substrate which carries the substrate at least at the coating station. A field shaping device can be provided by provision for the support surface to be held at a potential having the same sign as the potential of the coating material.

In the case of powder coatings, the apparatus can include a pretreatment station for supplying capture-enhancing liquid to the exposed surface of a substrate and a conveyor for conveying the substrate between the pretreatment station and the coating station, the pretreatment station being upstream of the coating station. The conveyor is preferably a drum. The apparatus preferably includes a heating station downstream of the coating station for using the powder or drying the liquid coating material on the substrate to a film.

In a third aspect, the invention provides a drum for the preferred apparatus of the invention.

In a fourth aspect, the invention provides a coated pharmaceutical having one coating on one face and a different coating, or no coating, on the other face. The coatings may be of different colours or of different polymers or biologically active materials.

The source of particulate coating material, whether powder or liquid, may be a multiple source comprising several sub-sources. The sub-sources can be of different colour coating materials or of coating materials containing different polymers. Thus, tablets having more than one colour on a single surface can be provided. The faces can be bicoloured or striped. Similarly, a tablet can carry two or more different polymer coatings, side by side.

In a fifth aspect, the invention provides a coated pharmaceutical the surface of at least one face of which is two or more adjacent different coatings. The coatings may be of different colours or of different polymer composition.

The substrate, such as the core of a pharmaceutical tablet, may be completely electrically isolated from its surroundings, for example in free fall. Preferably, however, while coating takes place the substrate is in contact with an electrode through which it is maintained at a potential (and to its surroundings). If the substrate is held on a support surface, such as the surface of a drum, it may sit in a depression in the surface. The surface of the depression can be of a conductive material and form part of the electrode. The support surface may be surrounded by an arrangement or insulating, conducting or semiconducting areas which act to shape the electrical field pattern. The substrate is thus surrounded by a potential well, to ensure that charged particles of coating material are attracted to it, rather than to the surroundings, including the support surface, if any, carrying the substrate.

BRIEF DESCRIPTION OF THE DRAWINGS

The invention will be further described, by way of example, with reference to the drawings, in which.

DESCRIPTION OF PREFERRED EMBODIMENTS

Figure 1:
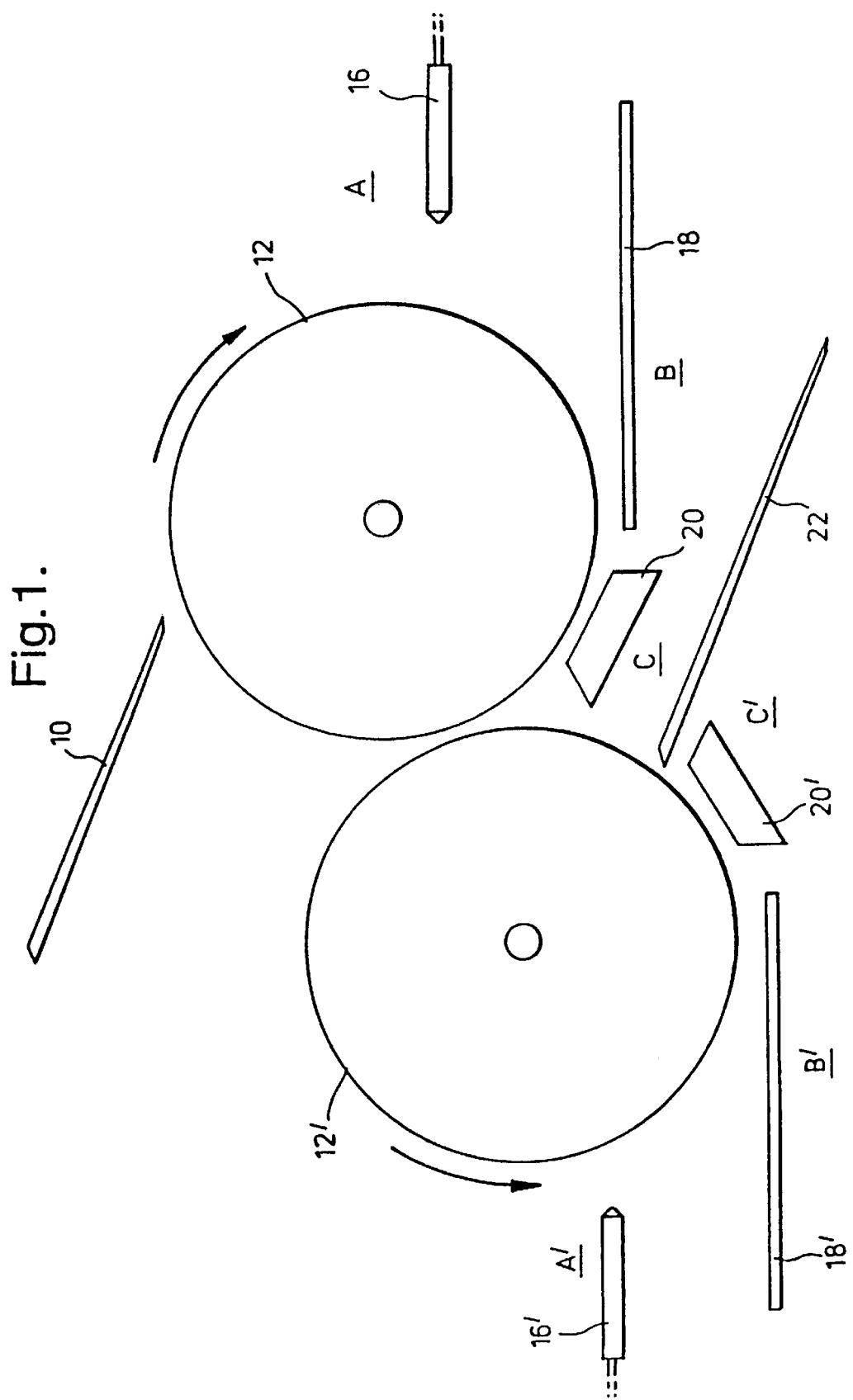
FIG. 1 shows schematically a preferred embodiment of apparatus according to the invention.

The apparatus shown schematically in FIG. 1 is for coating both sides of pharmaceutical tablet cores. The apparatus comprises an inclined tablet core feed chute 10 leading to a first rotatable drum 12. The drum 12 is of plastic with a steel surface and has circular depressions 14 (FIG. 2) in its outer surface in each of which a core can be held by vacuum, as will be explained later.

The drum 12 is rotatable in the direction shown by the arrow in FIG. 1. Adjacent the circumference of the drum 12 downstream of the tablet feed chute 10 is a pre-conditioning station A comprising an electrostatic spray gun 16, which produces charged droplets which are attracted to the substrate cores on the drum by reason of the potential difference between the droplets and the cores. Downstream of the preconditioning station A is a coating station B comprising a vibrating powder tray 18 for holding, fluidising and re-circulating the powder with which the cores are to be coated. Downstream of the coating station is a fusing station C comprising a heater 20. After the fusing station C, the coated core passes a cooling station, not shown, where cool air is directed over or around the core to cool the fused coating.

A second drum 12' is adjacent the first drum 12, the nip between the drums being downstream of the fusing station C and the cooling station. The second drum 12' rotates in the opposite sense to the first drum 12, as indicated by the arrow in FIG. 1. The second drum 12' is provided with a preconditioning station A' comprising a gun 16', a coating station B' comprising a powder tray 18', a fusing station C' comprising a heater 20' and a cooling station (not shown).

A core collection chute 22 inclines away from the second drum 12' downstream of the fusing station C', taking coated cores to be further processed and packed.

Figure 2:
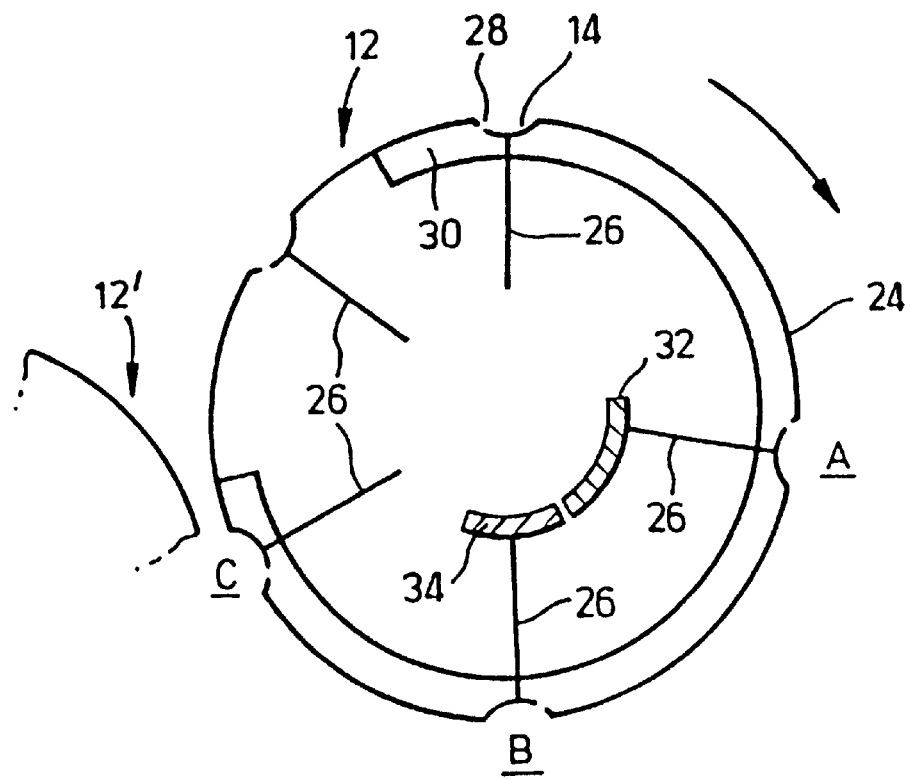
FIG. 2 shows diagrammatically a cross-section of a drum of the apparatus of FIG. 1.

The first drum 12 will be described in more detail with reference to FIG. 2. It comprises a rotatable shell 24, the outer face of which carries the depressions 14. in FIG. 2, only five exemplary depressions 14 are shown; it will be appreciated that in practice there will usually be more depressions, evenly spaced in a circumferential row around the shell 24, and that there may be several circumferential rows across the width of the drum, whether formed by one continuous shell or several contiguous shells. The depressions 14 on the drums are shaped and dimensioned to ensure that the complete face of the core and half the depth of the side wall is coated while the core is on one drum. In the case of a circular tablet core, a depression diameter close to that of the core diameter is preferred. In some applications, the depth of the depression should be such as to allow at least 50% of the core thickness to be exposed to the particles of the coating material so that exposure of first one face of the core and then the other leads to complete coverage of the core.

The surface of each depression 14 is electrically insulated from the surfaces of other depressions on the drum and is provided with a pick up arm 26 extending radially inward, toward but ending short or the centre of the drum. The pick up arms 26 are attached to the inner surface of the shell 24 and rotate with it. The pick up arm 26 and the depression 14 together make a moving electrode to charge a core in a depression. Each depression 14 has means for holding the core against forces such as gravity, for example a passage 28 through its wall which can be in communication with a vacuum manifold 30 which extends around a portion of the periphery of the drum interior from immediately upstream of the core feed chute 10 to adjacent the nip between the first drum 12 and the second drum 12'.

A first, earthed, stationary arcuate electrode 32 is located inside the drum at an angular position corresponding to the preconditioning station A. A second stationary arcuate electrode 34 at a potential is located inside the drum at an angular position corresponding to the coating station B. The outer arcuate surfaces of the stationary electrodes are at the same radial distance from the centre of the drum as the free ends of the pick up arms 26 of the moving electrodes. As the shell 24 rotates, the moving electrodes contact the first and second stationary electrodes sequentially.

The drum 12 is held at a potential having the same sign as the potential of the coating powder.

The second drum 12' is constructed similarly to the first drum, comprising a rotatable shell with depressions, pick up arms, first and second stationary electrodes and a vacuum manifold. The angular locations of the first and second stationary electrodes correspond to the second preconditioning station A' and the second coating station B', and the vacuum manifold extends from immediately upstream of the nip between the two drums to adjacent the core collection chute 22.

In use, cores are fed continuously to he core feed chute 10. A core passes down the core feed chute 10 into a depression 14 in the rotating shell 24 of the first drum 12. At that angular position, the depression overlies the vacuum manifold 30, and so the core is held in the depression by the vacuum through the passage 28 in the shell. The shell 24 continues to rotate bringing the core to the preconditioning station A, at which point the pick up arm 26 attached to the depression 14 contacts the first stationary electrode 32, earthing the moving electrode and thus the core held in the depression. As the earthed tablet core passes the electrostatic spray gun 16, its exposed surface is sprayed with charged droplets of a capture-enhancing liquid, for example polyethylene glycol.

The shell 24 continues to rotate, taking the moving electrode 26 out of contact with the first stationary electrode 32 and bringing it into contact with the second stationary electrode 34, as the tablet core approaches the coating station B. The exposed polyethylene glycol treated core surface is now at a potential difference to earth, and coating powder is attracted to it from the powder tray 18. The potential well generated by holding the surface of the drum and the powder at the same potential as each other and the core at a different potential ensures that powder is attracted substantially only to the core and that the surface of the drum remains substantially free of powder.

The shell 24 continues to rotate, taking the moving electrode 26 out of contact with the second stationary electrode 34 and bringing the core to the fusing station C, where the heater 20 fuses the powder on the coated surface of the core to form an effectively continuous film.

As the shell 24 continues to rotate, the core leaves the fusing station C, passes through the cooling station (not shown), so that the depression carrying the core no longer overlies the vacuum manifold 30. The core drops from the first drum 12 into a depression on the outer surface of the second drum 12', with its uncoated surface uppermost; the depression is in communication with the vacuum manifold of the second drum. The coating of the core is completed as it travels past the second preconditioning A', coating B' and fusing C' stations. The coating powder at the second coating station may be the same as that at the first, or different. Thus, tablets having differently coated surfaces can be produced. Such dissimilar coatings can be used to provide functionally modified behavior such as altered diffusion or dissolution controlled drug release or cosmetically different coatings such as those which would produce a bicoloured tablet. As the coated tablet draws adjacent the collection chute 22, the depression carrying it ceases to overlie the vacuum manifold, and the tablet falls into the chute and is further processed and packed.

The drums themselves are preferably at least 60 mm in diameter and not less than the minimum tablet diameter in width, rotating at least ½ r.p.m. The pressure in the vacuum manifold is sufficiently low to hold the tablet against gravity, preferably between 0.2 and 0.6 bar absolute.

In the electrostatic spray guns 16,16' at the preconditioning stations A,A', a semiconducting, non-volatile fluid, such as polyethylene glycol or an in aqueous solution thereof is fed at a rate of 0.1 to 1 ml/min. to a steel capillary of internal diameter of 0.05 to 2 mm. The capillary is connected to a current limited high voltage (up to 50 kV at 30 to 100 $\mu$A) potential as each core on a drum passes the gun, and a mist of charged droplets is discharged from the capillary toward the core on the drum. Since the cores on the drums are earthed at the preconditioning stations, the charged droplets are guided by the electric field between the capillary and the core to the exposed surface of the core, where they are captured. The cores may be held at a potential at the preconditioning stations, providing that they are also at a potential difference to the capillaries. In this case, the first stationary arcuate electrode 32 is at a potential. The supply of droplets from each capillary is controlled by switching the voltage off and earthing the capillary through a resistor (1 to 10 M$\Omega$) as each core leaves the preconditioning station. This ensures a sharp cut off of the droplets between tablet cores.

The pre-conditioning step may not always be required.

At coating stations B,B', powdered coating material is supplied by vibrating feeders to the vibrating trays 18,18'. The level of the powder in the trays is determined by a leveling blade above each tray. The powder may be vibrofluidized and continuously recirculated. The trays may be of a plastics material having an earthed metal strip under the arc swept by the tablet cores on the respective drums or they may be metallic trays. An alternative way to charge the particles is triboelectrical charging. The trays are preferably 50 to 150 mm long and 3 to 40 mm wide. If more than one tray is used, to provide a bi- or multicoloured face or a face carrying more than one polymer composition, the tray dimensions will be appropriately different. The tablet cores are charged by a voltage of −3 to −15 kV current limited to 5 $\mu$A.

A preferred powder coating composition is:
 46.5% by weight EUDRAGIT (RS ammoniomethacrylate co-polymer)
 28.0% by weight KLUCEL (hydroxy propyl cellulose)
 15.0% by weight titanium dioxide
 5.0% by weight aluminium lake
 5.0% by weight polyethylene glycol 6000
 0.5% by weight AEROSIL (200 colloidal silicon dioxide)

Another preferred powder coating composition is:
 39.75% by weight EUDRAGIT RS ammoniomethacrylate co-polymer
 39.75% by weight KLUCEL (hydroxypropylcellulose)
 15.0% by weight Titanium dioxide
 5.0% by weight Aluminium lake
 0.5% by weight AEROSIL (colloidal silicon dioxide)

The components are premixed under high shear, then wet granulated by mixing under high shear with water (10–15% by weight). The granulated mixture is dried in fluid bed drier at about 45° C. for 20 to 30 minutes to reduce the moisture content to below 3% by weight. The dried granules are milled and micronised to a powder having a size distribution such that 50% by volume of the particles are of a size less than 20 $\mu$m, and about 100% by volume are of a size less than 60 $\mu$m. The peak size is about 10 $\mu$m.

Figure 3:
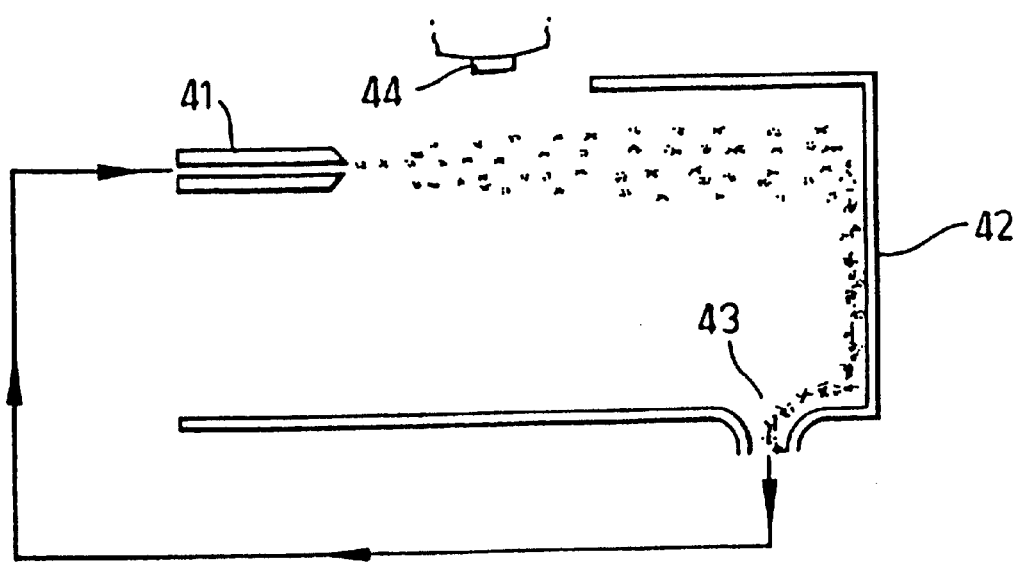
FIG. 3 shows diagrammatically means for providing droplets of liquid coating material for an apparatus according to the invention.

If the particulate coating material is liquid droplets, the apparatus is of a similar construction to that for applying powdered coating material to the cores. The vibrating trays holding the powder are replaced by means for producing liquid droplets with low momentum, such as that shown in FIG. 3. The apparatus may be designed so that a source of powder coating material may be easily replaced by a source of droplets of liquid coating material.

Droplets are produced by a spray gun 41 held at earth potential and electrically connected to the drum (12). The gun may be formed of metal or a polymer material. The direction of the spray is towards a baffle 42 down which the coalesced droplets can run into a re-circulating reservoir 43. The spray gun 41 produces a spray of relatively high initial momentum. This impinges on an internal baffle which breaks the spray up into a mist of droplets of low momentum. The momentum of the droplets produced by the spray gun is mainly in a direction normal to the substrate 44. If the substrate is uncharged there will be effectively no droplet capture onto the substrate surface. When the charge is applied to the substrate surface the droplets are attracted thereto to form a coating thereon which is later dried at a drying station similar to the fusing station C of the powder treatment apparatus. The pre-conditioning step A may be omitted in the case of liquid coating material.

A preferred liquid coating composition comprises:
hydroxyprozylmethylcellulose 70%
glycerol 7%
iron oxide yellow 23%
in aqueous dispersion.

At the fusing or drying stations C,C', energy is imparted to the core surfaces to fuse the powder or dry the liquid and provide a uniform coating on the exposed surfaces of the core. The energy is provided by focused radiation preferably in the infra-red region; the energy power requirement will be determined largely by the coating material. After fusing or drying, the coating is set by cooling, using an air blower.

Preferred coating apparatus according to the invention can coat up to 300,000 tablet cores each hour.

What is claimed is:

1. A method of electrostatically coating a pharmaceutical substrate comprising bringing the substrate to a coating station at which it is held substantially electrically isolated from its surroundings adjacent a source of particulate coating material, the substrate and the coating material being held at a potential difference to each other sufficient to coat the exposed surface of the substrate with particles of coating material.

2. A method according to claim 1 in which the substrate is at a potential difference to its surroundings.

3. A method according to claim 1 in which the electric field between the coating material and the substrate is such that the substrate is in a potential well.

4. A method according to claim 1 in which at the coating station the substrate is supported by but electrically isolated from a support surface.

5. A method according to claim 4 in which the potential difference to earth of the support surface and of the coating material are of the same sign.

6. A method according to claim 4 in which the support surface is at the same potential as the coating material.

7. A method according to claim 1 in which the substrate is held at the coating station at a potential different from that of earth.

8. A method according to claim 1 in which substantially the only force tending to cause movement of the coating material towards the substrate is an electrostatic force.

9. A method according to claim 1 in which the substrate is supported, and in electrical contact with an electrode, the substrate being otherwise electrically isolated from its surroundings.

10. A method according to claim 9 in which a plurality of substrates are supported on respective ones of plurality of electrodes electrically isolated from each other and forming part of a support surface.

11. A method according to claim 10 in which the support surface is continuous.

12. A method according to claim 1 in which the coating material particles are at a potential different from that of earth.

13. A method according to claim 1 in which a powdered coating material is used.

14. A method according to claim 13 further comprising bringing the substrate coated with powder to a fusing station where the powder on the substrate is fused to a uniform coating.

15. A method according to claim 14 in which the fusing is by heating.

16. A method according to claim 15 in which the heating is by infra-red radiation.

17. A method according to claim 14 further comprising cooling the fused coating on the substrate.

18. A method according to claim 13 further comprising, prior to bringing the substrate to the coating station, bringing the substrate to a preconditioning station at which the exposed surface of the substrate is coated with a capture-enhancing liquid.

19. A method according to claim 18 in which the coating carried out at the preconditioning station is electrostatic coating.

20. A method according to claim 4 wherein said support surface is electrically conductive.

21. A method according to claim 1 in which the coating material is liquid.

22. A method according to claim 1 in which the substrate is carried by a support surface having a plurality of individual locations the substrate being held at are of those locations, electrically isolated from the remainder of the surface, and at a potential different from that of earth.

23. A method according to claim 1 in which the substrate is held in contact with an electrode at least while it is at the coating station.

24. A continuous method according to claim 1 in which the substrate is carried by the surface of a rotating drum.

25. A method according to claim 1 further comprising turning the substrate after application of a coating to a first surface of the substrate and applying a coating to a second surface of the substrate.

26. A method according to claim 1 in which the coating material comprises a biologically active material.

27. A method of producing a plurality of coated pharmaceutical substrates, each comprising a substrate electrostatically coated by coating material, the method comprising:

carrying the substrates on a support surface to a coating station at which they are held adjacent a source of particulate coating material, each substrate being in electrical contact with an electrode at least while it is at the coating station, but otherwise electrically isolated from its surroundings; and holding the substrates and the coating material at a potential difference to each other sufficient to coat the exposed surface of each substrate.

28. A method according to claim 27 in which the substrates and the electrode are at a potential difference to their surroundings.

29. A method according to claim 27 in which the support surface is electrically conductive.

30. A method according to claim 29 in which the potential difference to earth of the support surface and of the coating material are of the same sign.

31. A method according to claim 29 in which the support surface is at the same potential as the coating material.

32. A method according to claim 27 in which the substrates are held at the coating station at a potential different from that of earth.

33. A method according to claim 27 in which the substrates are supported on, and in electrical contact with, respective ones of a plurality of electrodes, each electrically isolated from each other and forming part of the support surface.

34. A method according to claim 27 in which the coating material particles are at a potential different from that of earth.

35. A method according to claim 27 in which a powdered coating material is used.

36. A method according to claim 35 further comprising bringing the substrates coated with powder to a fusing station where the powder on the substrates is fused to a uniform coating.

37. A method according to claim 27 in which the coating material is liquid.

38. A method according to claim 27 in which the support surface has a plurality of individual locations which are electrically isolated from the remainder of the surface, each substrate being associated with one of those locations, and being held at that location at a potential different from that of earth.

39. A continuous method according to claim 27 in which the substrates are carried by the surface of a rotating drum.

40. A method according to claim 27 further comprising turning the substrates after application of a coating to a first surface of the substrates and applying a coating to a second surface of the substrates.

41. A method according to claim 27 in which the coating material comprises a biologically active material.

42. A method of producing a plurality of coated pharmaceutical substrates, each comprising a substrate electrostatically coated by coating material, the method comprising:
carrying the substrates on a support surface to a coating station at which they are held adjacent a source of particulate coating material, each substrate being associated with an individual location provided on the support surface which is electrically isolated from the remainder of the surface; and
holding the substrates and the coating material at a potential difference to each other sufficient to coat the exposed surface of each substrate.

43. A method according to claim 42 in which the substrates are at a potential difference to the remainder of the surface.

44. A method according to claim 42 in which the support surface is electrically conductive.

45. A method according to claim 42 in which the potential difference to earth of the support surface and of the coating material are of the same sign.

46. A method according to claim 42 in which the support surface is at the same potential as the coating material.

47. A method according to claim 42 in which the substrates are held at the coating station at a potential different from that of earth.

48. A method according to claim 42 in which the substrates are supported on, and in electrical contact with, respective ones of a plurality of electrodes, each electrically isolated from each other and forming part of the support surface.

49. A method according to claim 42 in which the coating material particles are at a potential different from that of earth.

50. A method according to claim 42 in which a powdered coating material is used.

51. A method according to claim 42 further comprising bringing the substrates coated with powder to a fusing station where the powder on the substrates is fused to a uniform coating.

52. A method according to claim 42 in which the coating material is liquid.

53. A method according to claim 42 in which the substrates are held in contact with an electrode at least while they are at the coating station.

54. A continuous method according to claim 42 in which the substrates are carried by the surface of a rotating drum.

55. A method according to claim 42 further comprising turning the substrates after application of a coating to a first surface of the substrates and applying a coating to a second surface of the substrates.

56. A method according to claim 42 in which the coating material comprises a biologically active material.

57. A method of producing a plurality of tablet cores, each comprising a tablet core electrostatically coated by coating material, the method comprising:
carrying the tablet cores on a support surface to a coating station at which they are held adjacent a source of particulate coating material, each tablet core being associated with an individual location provided on the support surface which is electrically isolated from the remainder of the support surface;
holding the tablet cores and the coating material at a potential difference to each other sufficient to coat the exposed surface of each table core.

58. A method according to claim 57 in which the tablet cores are at a potential difference to the remainder of the support surface.

59. A method according to claim 57 in which the support surface is electrically conductive.

60. A method according to claim 57 in which the potential difference to earth of the support surface and of the coating material are of the same sign.

61. A method according to claim 57 in which the support surface is at the same potential as the coating material.

62. A method according to claim 57 in which the tablet cores are held at the coating station at a potential different from that of earth.

63. A method according to claim 57 in which the tablet cores are supported on, and in electrical contact with, respective ones of a plurality of electrodes, each electrically isolated from each other and forming part of the support surface.

64. A method according to claim 57 in which the coating material particles are at a potential different from that of earth.

65. A method according to claim 57 in which a powdered coating material is used.

66. A method according to claim 65 further comprising bringing the tablet cores coated with powder to a fusing station where the powder on the tablet cores is fused to a uniform coating.

67. A method according to claim 57 in which the coating material is liquid.

68. A method according to claim 57 in which the tablet cores are held in contact with an electrode at least while they are at the coating station.

69. A continuous method according to claim 57 in which the tablet cores are carried by the surface of a rotating drum.

70. A method according to claim 57 further comprising turning the tablet cores after application of a coating to a first surface of the tablet cores and applying a coating to a second surface of the tablet cores.

71. A method of producing a plurality of coated tablet cores, each comprising a tablet core electrostatically coated by coating material, the method comprising:
carrying the tablet cores on a support surface to a coating station at which they are held adjacent a source of particulate coating material, each tablet core being in electrical contact with an electrode at least while it is at the coating station, but otherwise electrically isolated from its surroundings; and
holding the tablet cores and the coating material at a potential difference to each other sufficient to coat the exposed surface of each tablet core.

72. A method according to claim 71 in which the tablet cores and the electrode are at a potential difference to their surroundings.

73. A method according to claim 71 in which the support surface is electrically conductive.

74. A method according to claim 71 in which the potential difference to earth of the support surface and of the coating material are of the same sign.

75. A method according to claim 71 in which the support surface is at the same potential as the coating material.

76. A method according to claim 71 in which the tablet cores are held at the coating station at a potential different from that of earth.

77. A method according to claim 71 in which the tablet cores are supported on, and in electrical contact with, respective ones of a plurality of electrodes, each electrically isolated from each other and forming part of the support surface.

78. A method according to claim 71 in which the coating material particles are at a potential different from that of earth.

79. A method according to claim 71 in which a powdered coating material is used.

80. A method according to claim 79 further comprising bringing the tablet cores coated with powder to a fusing station where the powder on the tablet cores is fused to a uniform coating.

81. A method according to claim 71 in which the coating material is liquid.

82. A method according to claim 71 in which the support surface has a plurality of individual locations which are electrically isolated from the remainder of the surface, each substrate being associated with one of those locations, and being held at that location at a potential different from that of earth.

83. A continuous method according to claim 71 in which the tablet cores are carried by the surface of a rotating drum.

84. A method according to claim 71 further comprising turning the tablet cores after application of a coating to a first surface of the substrates and applying a coating to a second surface of the tablet cores.

* * * * *

UNITED STATES PATENT AND TRADEMARK OFFICE
CERTIFICATE OF CORRECTION

PATENT NO. : 6,117,479
DATED : September 12, 2000
INVENTOR(S) : Hogan et al.

It is certified that error appears in the above-identified patent and that said Letters Patent is hereby corrected as shown below:

On title page of the patent, left-hand column, below " Foreign Application Priority Data" insert --May 8, 1996 PCT/GB96/01102--.

Signed and Sealed this

Twelfth Day of June, 2001

*Attest:*

*Attesting Officer*

NICHOLAS P. GODICI
*Acting Director of the United States Patent and Trademark Office*